(12) United States Patent
Han et al.

(10) Patent No.: US 10,898,138 B2
(45) Date of Patent: Jan. 26, 2021

(54) FLEXIBLE PATCH INCLUDING A PLURALITY OF THROUGH HOLES WHICH CAN BE ADHERED TO SKIN AND METHOD FOR MANUFACTURING THE SAME

(71) Applicants: AMOREPACIFIC CORPORATION, Seoul (KR); MASSACHUSETTS INSTITUTE OF TECHNOLOGY, Cambridge, MA (US)

(72) Inventors: Jiyeon Han, Yongin-si (KR); Han-Wool Yeun, Cambridge, MA (US); Eunjoo Kim, Yongin-si (KR); Jeehwan Kim, Cambridge, MA (US)

(73) Assignees: AMOREPACIFIC CORPORATION, Seoul (KR); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 71 days.

(21) Appl. No.: 16/223,623

(22) Filed: Dec. 18, 2018

(65) Prior Publication Data

US 2020/0187858 A1 Jun. 18, 2020

(51) Int. Cl.
| | |
|---|---|
| *B44C 1/22* | (2006.01) |
| *A61B 5/00* | (2006.01) |
| *B01D 67/00* | (2006.01) |
| *B32B 3/26* | (2006.01) |
| *B32B 3/30* | (2006.01) |

(52) U.S. Cl.
CPC ............ *A61B 5/6833* (2013.01); *A61B 5/442* (2013.01); *A61B 5/6834* (2013.01); *A61B 2562/028* (2013.01); *B32B 3/266* (2013.01); *B32B 3/30* (2013.01); *B32B 2405/00* (2013.01)

(58) Field of Classification Search
None
See application file for complete search history.

(56) References Cited

U.S. PATENT DOCUMENTS

| | | | | |
|---|---|---|---|---|
| 2014/0303452 | A1* | 10/2014 | Ghaffari | A61B 5/03 600/301 |
| 2015/0351689 | A1* | 12/2015 | Adams | A61B 5/6833 600/300 |

FOREIGN PATENT DOCUMENTS

KR 101746492 6/2017

OTHER PUBLICATIONS

Akihito Miyamoto, et al., "Inflammation-free, gas-permeable, lightweight, stretchable on-skin electronics with nanomeshes", Nature Nanotechnology, vol. 12, (2017), pp. 1-8.

(Continued)

*Primary Examiner* — Shamim Ahmed
(74) *Attorney, Agent, or Firm* — Cantor Colburn LLP

(57) ABSTRACT

Exemplary embodiments relate to a skin-adherable flexible patch including a flexible patch layer having one surface that can adhere to skin and configured to support a micro scale semiconductor device; and a plurality of holes passing through from one surface of the flexible patch to the other surface of the flexible patch, and a method for manufacturing the flexible patch.

9 Claims, 12 Drawing Sheets

(56) References Cited

OTHER PUBLICATIONS

Angelo Landriscina, et al., "Nanotechnology, Inflammation and the Skin Barrier: Innovative Approaches for Skin Health and Cosmesis", Cosmetics, (2015), vol. 2, pp. 177-186.
Canan Dagdeviren, et al., "Conformal piezoelectric systems for clinical and experimental characterization of soft tissue biomechanics", Nature Materials, vol. 14, (Jul. 2015), pp. 728-736.
Moon Kee Choi et al., "Cephalopod-Inspired Miniaturized Suction Cups for Smart Medical Skin", Adv. Healthcare. Mater., vol. 5, (2015), pp. 1-33.

* cited by examiner

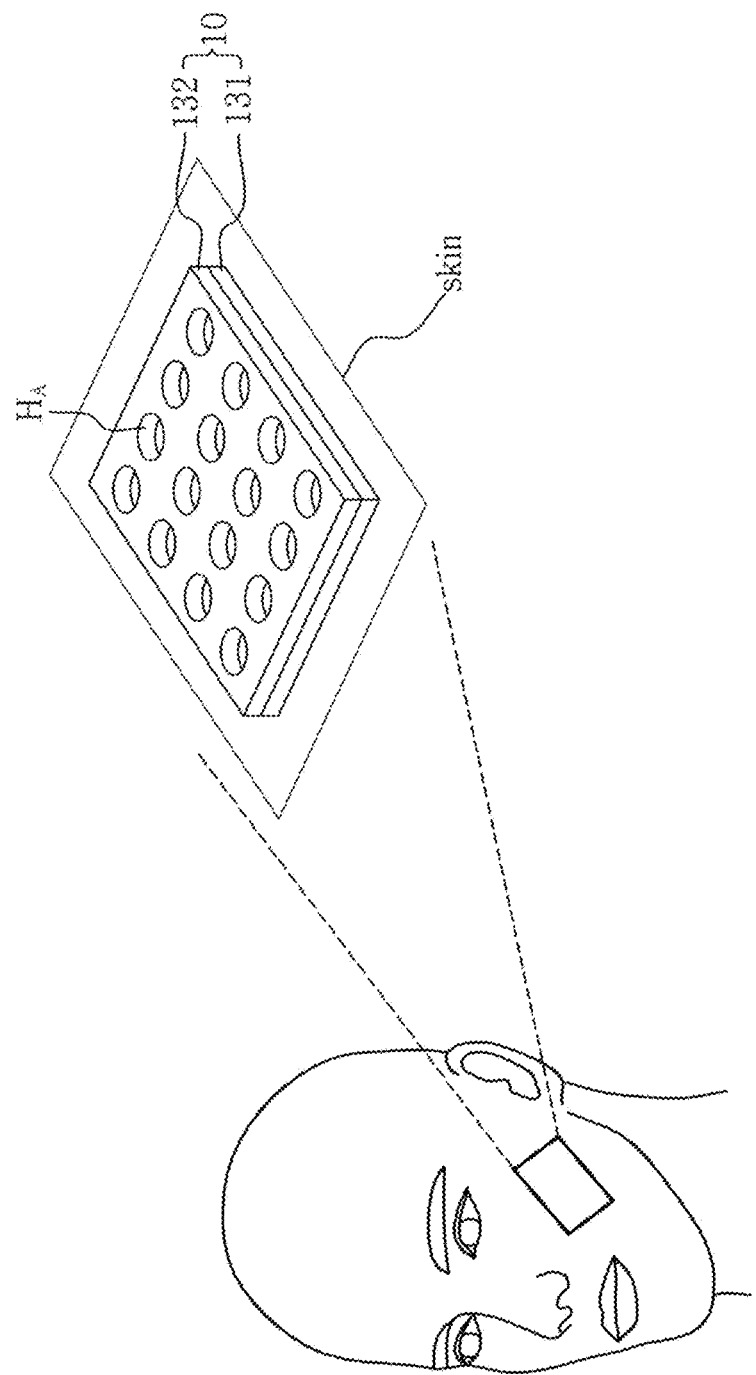

furrow

FLEXIBLE PATCH INCLUDING A PLURALITY OF THROUGH HOLES WHICH CAN BE ADHERED TO SKIN AND METHOD FOR MANUFACTURING THE SAME

BACKGROUND

1. Field

Exemplary embodiments relate to a skin-adherable flexible patch, and more particularly, to a skin-adherable flexible patch having a micro through-hole patterned surface with strong adhesiveness to skin and high air permeability and a method for manufacturing the same.

2. Description of the Related Art

As the industrial and economic development improves the quality of life, a majority of modern people desire younger-looking and more beautiful faces and bodies simply beyond healthy living. To meet the modern people's desires, there is an increasing interest in skin-conformable electronic sensing technology (such as, for example, skin sensors) that enables continuous monitoring of health conditions, in particular, skin conditions.

In general, to acquire information associated with skin such as skin changes and conditions, a skin sensor is adhered to a target's skin. However, skin is an outer covering organ that is disposed at the outermost of human body and has the largest area, and skin does a variety of pore-based physiological behaviors, such as sweat, sebum secretion and volatile organic excretion, essential to preserving homeostasis in the human body made up of compounds. A skin sensor that adheres to skin should be manufactured, considering the above-described biological properties of skin.

Accordingly, high quality skin sensors for monitoring long-term health conditions or skin conditions need to have both adhesiveness and air permeability as essential requirements.

The conventional skin sensors are manufactured using a polymer substrate of PI or PET having poor permeability, so they have posed the problem: when a skin sensor is adhered to skin, the skin sensor blocks the skin pores and inhibits the physiological behaviors of skin, causing inflammation and irritation. When a chemical adhesive is additionally used for strong adhesion between the skin sensor and the skin, inflammation may become worse. The infected skin loses the protection function against viruses, which may cause secondary inflammation or complications. Additionally, due to the elastic modulus of the polymer substrate that is about 1000 times higher than the skin, the adhesive strength to the skin is very low, failing to adhere to the skin for a long term, or resulting in very low efficiency of re-adhesion.

To overcome this problem, attempts have been made to develop skin sensors of which a surface that adheres to skin has a micro structure such as octopus suckers or gecko feet based on elastomer including PDMS that is similar to the mechanical properties of skin, but the micro structure is a non-penetrating structure that only exists on the surface. Accordingly, the manufacturing process is complex, and it is difficult to reduce the size.

RELATED LITERATURES

Patent Literatures (Patent Literature 1) KR 10-1746492 B1

SUMMARY

According to an aspect of the present disclosure, there is provided a flexible patch having a micro-hole patterned surface with a high adhesive strength to skin and high air permeability.

Further, there is provided a method for manufacturing the flexible patch.

In an aspect, a skin-adherable flexible patch, comprising: a first flexible layer having one surface that can adhere to the skin; a second flexible layer that is more rigid than the first flexible layer; and a plurality of holes passing through from one surface of the flexible patch to the other surface of the flexible patch.

In an embodiment, wherein the first flexible layer and the second flexible layer include a pre-polymer and a curing agent, and a curing agent ratio of the second flexible layer is higher than a curing agent ratio of the first flexible layer.

In an embodiment, wherein spacing between the plurality of holes is less than 60 μm.

In an embodiment, wherein the first flexible layer or the second flexible layer is made of a material including polydimethylsiloxane (PDMS).

In an embodiment, wherein the flexible patch includes a plurality of circular holes.

In an embodiment, wherein the flexible patch further includes a plurality of dumbbell-shaped holes.

In an embodiment, wherein a thickness (t1) of the first flexible layer and a thickness (t2) of the second flexible layer are determined based on the following Equation:

$$W \geq Wc \text{ where } Wc = Eeqt^3/(24R^2),$$

$$W = \frac{4\gamma_{dPatch}\gamma_{dskin}}{\gamma_{dPatch} + \gamma_{dskin}} \frac{4\gamma_{pPatch}\gamma_{pskin}}{\gamma_{pPatch} + \gamma_{pskin}},$$

$$E_{eq} = \left(\frac{t_1}{t_1 + t_2}\right)E_1 + \left(\frac{t_2}{t_1 + t_2}\right)E_2$$

$$t = t1 + t2,$$

where t denotes a thickness of the flexible patch, E1 denotes an elastic modulus of the first flexible layer, E2 denotes an elastic modulus of the second flexible layer, R denotes a curvature of the flexible patch adhered to the skin, $\delta_{dSkin}$ denotes a dispersive component of contact surface of the skin, $\delta_{dPatch}$ denotes a dispersive component of contact surface of the patch, $\gamma_{pSkin}$ denotes a polar component of contact surface of the skin, and $\delta_{pPatch}$ denotes a polar component of contact surface of the patch.

In another aspect, a method for manufacturing a skin-adherable flexible patch, comprising: forming a first sacrificial layer on a mold having a plurality of concave furrows on one surface; forming a flexible patch layer on the first sacrificial layer; contacting a board with the flexible patch layer, and rubbing the board or the flexible layer to remove a region of the flexible patch layer exceeding the furrows; and etching the first sacrificial layer to obtain a flexible patch having a plurality of holes.

In an embodiment, wherein in the removing the flexible patch layer, the board includes a substrate; and a second sacrificial layer formed on one surface of the substrate, the second sacrificial layer contacts the region of the flexible layer exceeding the furrows.

In an embodiment, wherein the removing the flexible patch layer further comprises heating the contact region.

In an embodiment, wherein the removing the flexible patch layer further comprises applying pressure to the contact region between the board and the region of the flexible layer exceeding the furrows.

In an embodiment, wherein the flexible patch layer is made of a material including poly-dimethylsiloxane (PDMS).

In an embodiment, wherein the forming the flexible patch layer comprises: forming a first flexible layer on the sacrificial layer; and forming a second flexible layer on the first flexible layer, the second flexible layer being more rigid than the first flexible layer.

In an embodiment, wherein a thickness (t1) of the first flexible layer and a thickness (t2) of the second flexible layer are determined based on the following Equation:

$$W \geq Wc \text{ where } Wc = Eeq t^3/(24R^2),$$

$$W = \frac{4\gamma_{dPatch}\gamma_{dskin}}{\gamma_{dPatch} + \gamma_{dskin}} \frac{4\gamma_{pPatch}\gamma_{pskin}}{\gamma_{pPatch} + \gamma_{pskin}},$$

$$E_{eq} = \left(\frac{t_1}{t_1 + t_2}\right)E_1 + \left(\frac{t_2}{t_1 + t_2}\right)E_2$$

$$t = t1 + t2,$$

where t denotes a thickness of the flexible patch, E1 denotes an elastic modulus of the first flexible layer, E2 denotes an elastic modulus of the second flexible layer, R denotes a curvature of the flexible patch adhered to the skin, $\gamma_{dSkin}$ denotes a dispersive component of contact surface of the skin, $\gamma_{dPatch}$ denotes a dispersive component of contact surface of the patch, $\gamma_{pSkin}$ denotes a polar component of contact surface of the skin, and $\gamma_{pPatch}$ denotes a polar component of contact surface of the patch.

In an embodiment, wherein the forming the first sacrificial layer comprises forming the first sacrificial layer by spin coating, and the first sacrificial layer is made of a material including poly(methyl methacrylate) (PMMA), and a surface of the mold has furrows that can form circular through-holes.

In an embodiment, wherein the forming the first sacrificial layer comprises forming the first sacrificial layer by evaporation coating, and the first sacrificial layer is formed with a self-assembled monolayer (SAM) structure, and a surface of the mold has furrows that can form circular through-holes and dumbbell through-holes.

As opposed to the conventional patch based on polymer that has different mechanical properties (e.g., elastic modulus and Poisson's ratio) from skin, the flexible patch including through-holes according to an aspect of the present disclosure uses a flexible material (e.g., PDMS) having similar mechanical properties (e.g., elastic modulus, Poisson's ratio) to skin, and does not have an interfacial mechanical mismatch when adhering to skin. As a result, buckling and delamination does not occur in the patch, thereby preventing damage in the patch. Additionally, the reduced adhesiveness caused by buckling and delamination is avoided, and the flexible patch has strong adhesiveness.

Further, the flexible patch has a plurality of holes patterned with a penetrating structure. When an external force is applied for adhesion to the skin surface, the skin is held in the holes, and accordingly the flexible patch can adhere to the skin surface. In particular, the holes of the flexible patch are of penetrating type, and the volume of skin held in the holes increases, ensuring strong adhesiveness.

Additionally, the holes are patterned with a smaller spacing than the size of sweat pores (e.g., general smallest sweat pores are 60 μm), ensuring high air permeability.

Additionally, the flexible patch may have a geometric plane (e.g., a plane in which dumbbell shapes and circular shapes are formed) that can implement an auxetic property, ensuring high skin conformability and stretchability.

The flexible patch may be used as a substrate used to manufacture a skin sensor. For example, in manufacturing a skin sensor having a piezoelectric resistance deformation sensing function to measure skin elasticity, the flexible patch may be used as a substrate onto which sensor circuits are integrated. However, the flexible patch is not limited thereto, and can be used as a substrate onto which semiconductor circuits having various functions may be integrated.

BRIEF DESCRIPTION OF THE DRAWINGS

To describe the technical solutions of the embodiments of the present disclosure or related art more clearly, drawings required for describing the embodiments will be briefly introduced below. To identify similar elements shown in one or more drawings, the same reference numeral is used. It should be understood that the accompanying drawings are provided for illustration purposes only, but not intended to limit the embodiments of the specification. Additionally, certain elements to which various modifications such as exaggeration and omission are applied may be shown in the accompanying drawings for clarity of description.

FIGS. 1A and 1B are schematic diagrams of a flexible patch that adheres to a subject's skin, according to embodiments of the present disclosure.

DETAILED DESCRIPTION

Figure 1B:
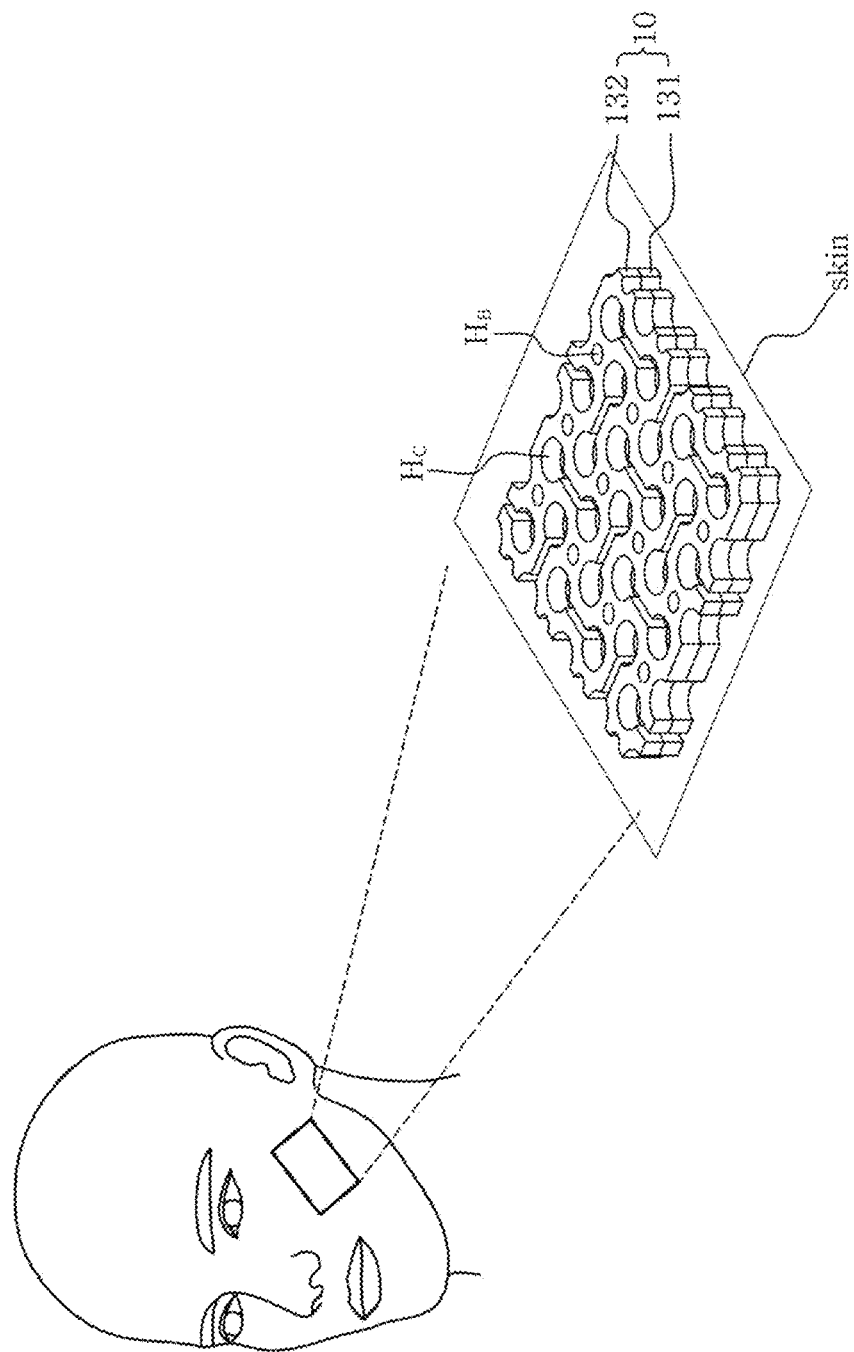

Hereinafter, the embodiments of the present disclosure will be described in detail with reference to the accompanying drawings.

It will be understood that, if an element is referred to as being "directly above" another element, it can be directly above the other element or intervening elements may be present. In contrast, if an element is referred to as being "directly above" another element, there are no intervening elements present.

The terms "first", "second", and the like are used to describe various parts, components, areas, layers and/or sections, but are not limited thereto. These terms are only used to distinguish one part, component, area, layer or section from another. Accordingly, a first part, component, region, layer or section stated below may be referred to as a second part, component, region, layer or section without departing from the scope of the present disclosure.

The terminology used herein is for the purpose of describing particular embodiments only and is not intended to be limiting of the present disclosure. As used herein, the singular forms are intended to include the plural forms as well, unless the context clearly indicates otherwise. It will be further understood that the terms "comprising" and "including" when used in this specification, specify the presence of stated features, regions, integers, steps, operations, elements, and/or components, but do not preclude the presence or addition of one or more other features, regions, integers, steps, operations, elements, and/or components.

Spatially relative terms (e.g., "beneath", "below", "above" and the like) may be used herein for ease of description in describing a relationship between one element and another as illustrated in the figures. It will be understood that these terms are intended to encompass the intended meaning in the figures as well as different meanings or operations of the device in use. For example, if the device in the figures is turned over, elements described as "below" or "beneath" other elements would then be oriented "above" the other elements. Thus, the term "below" can encompass both an orientation that is above, as well as, below. The device may otherwise rotate (90° or at any other angle) and the spatially relative terms should be interpreted accordingly.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

According to embodiments of the present disclosure, it is possible to manufacture a skin-adherable flexible patch having a plurality of through-holes. The flexible patch has strong adhesiveness, and thus can adhere to skin for a long time. Additionally, the flexible patch has high air permeability, and can minimize the influence on a user's skin and health when it adheres to skin even for a long time.

Hereinafter, the embodiments of the present disclosure will be described in detail with reference to the accompanying drawings.

FIGS. 1A and 1B are schematic diagrams of a flexible patch that adheres to a subject's skin according to the embodiments of the present disclosure.

Referring to FIGS. 1A and 1B, the flexible patch 10 is a substrate onto which a semiconductor circuit unit is integrated, and is configured such that at least one surface has sufficient viscosity to adhere to skin. Additionally, the flexible patch 10 includes a plurality of through-holes with high air permeability and strong adhesiveness.

In the flexible patch 10 according to the embodiments, a skin-adhering region 131 has viscosity, and a different region 132 has higher rigidity. For example, the skin-adhering region 131 has a lower elastic modulus, and the different region 132 has a higher elastic modulus than the skin-adhering region 131. In another embodiment, the flexible patch 10 may have two or more layers. This will be described in more detail with reference to the following S130.

In an embodiment, the flexible patch 10 may include a first through-hole pattern to obtain strong adhesiveness and high air permeability. The hole of the first through-hole pattern has a circular plane, and is a hole HA passing through the cross section of the flexible patch 10.

In an embodiment, the spacing between each through-hole is less than 60 μm. In certain embodiments, the spacing between each through-hole may be 50 μm.

The first through-hole pattern may have a combination of circular through-holes. In some embodiments, as shown in the FIG. 1A, the first through-hole pattern may have a repeated arrangement of circular through-holes of the same size on the surface of the flexible patch 10. In the other embodiments, the first through-hole pattern may have a combination of various arrangements of circular through-holes of different sizes on the surface of the flexible patch 10. For example, the first through-hole pattern may have certain patterns repeated on the surface of the flexible patch 10, which has a combination of circular through-holes having a larger diameter at the center of the certain pattern and circular through-holes having a smaller diameter surrounding the lager through-hole.

In another embodiment, the flexible patch 10 may include a second through-hole pattern forming a geometric plane that can have an auxetic structure property. In the above embodiment, the second through-hole pattern includes a through-hole $H_C$ having circular through-holes $H_B$ at two ends and a connector connecting the two ends. Each end of the through-hole $H_C$ is circular, and the connector is a rectangular dumbbell-shaped through-hole (hereinafter, dumbbell through-hole).

In the second through-hole pattern, the spacing between the dumbbell through-hole $H_C$ and the dumbbell through-hole $H_C$, the spacing between the dumbbell through-hole $H_C$ and the circular through-hole $H_B$, and the spacing between the circular through-hole $H_B$ and the circular through-hole $H_B$ may be 60 μm or less.

In an example, in the flexible patch 10 including the second through-hole pattern as shown in FIG. 1B, the spacing between the center of a connector of one dumbbell through-hole $H_C$ and one end of another dumbbell through-hole $H_C$ may be 35 μm, and the spacing between one end of one dumbbell through-hole $H_C$ and another circular through-hole $H_B$ may be 25 μm. Additionally, the diameter of the circular through-hole $H_B$ may be 50 μm, and the inner spacing of one end of the dumbbell through-hole $H_C$ may be 100 μm. However, this is for illustration purposes only, and may be variously set based on air permeability, adhesiveness and durability of the flexible patch 10.

The flexible patch 10 has similar mechanical properties to skin, and has strong adhesiveness and (nearly 100%) high air permeability. The flexible patch 10 adheres to skin by the viscosity of the region 131, and skin is held in the through-holes. Accordingly, the flexible patch 10 can have strong adhesiveness. Additionally, the hole, in which skin is held, is a through-hole passing through the cross section of the flexible patch 10, ensuring high air permeability.

Additionally, parts have somewhat of high elastic modulus and sufficiently support the semiconductor circuit, and can be used to manufacture small electronic devices that need to be adhered to skin.

First Embodiment

Figure 2:
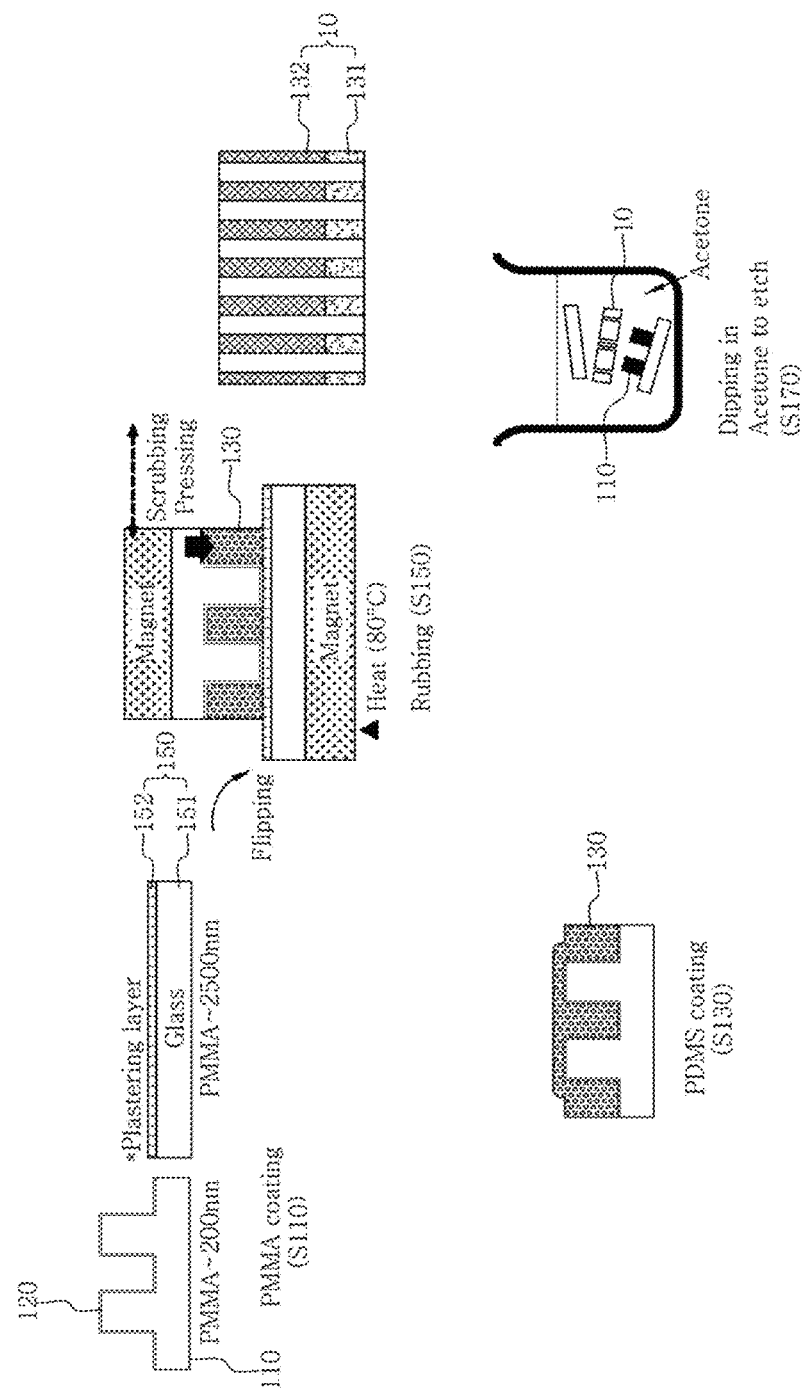
FIG. 2 is an exemplary conceptual diagram of a method for manufacturing a flexible patch, according to a first embodiment of the present disclosure.

FIG. 2 is a schematic conceptual diagram showing a process of manufacturing the flexible patch according to a first embodiment of the present disclosure.

Referring to FIG. 2, the method for manufacturing the flexible patch 10 according to the first embodiment includes forming a sacrificial layer on a mold having a plurality of concave furrows on one surface (S110); and forming a flexible patch layer on the sacrificial layer (S130).

For the rigid material, as shown in FIG. 1, a wet/dry etching method is used to form a geometric plane structure such as a micro-hole patterned surface. However, when a flexible material (e.g., PDMS, etc.) that is relatively soft is used to form a geometric plane structure using a dry/wet etching method, the geometric plane structure such as holes is out of shape. However, when a mold 110 having a plurality of concave furrows is used to form a plurality of holes on one surface of the flexible material, it is possible to obtain a flexible patch layer 130 having the holes that are not put out of shape.

The mold 110 has a plurality of furrows formed on one surface, and thus has a geometric plane. The cross section of the furrows that form the geometric plane of the mold 110 is concave inward one surface as shown in FIG. 2. When any flowable material (e.g., including the flexible material used to form the flexible patch layer 130) is formed on the mold 110, the material fills the furrows. When the material is cured, a height structure corresponding to the filled furrows is formed in the furrows. The furrows may have a single step or one or more steps.

The flexible patch layer 130 includes a material layer that is sticky enough to adhere to skin. Accordingly, when the flexible patch layer 130 is formed immediately on the mold 110, it is difficult to separate the flexible patch layer 130 from the mold 110, and when damage occurs in the flexible patch layer 130 in this process, there is a risk that the quality of the flexible patch 10 may be degraded. To overcome this problem, before filling the furrows of the mold 110 with the flexible material, a sacrificial layer 120 having an anti-sticky layer function to prevent the adhesion between the flexible patch layer 130 and the mold 110 is formed between the mold 110 and the flexible patch layer 130 (S110). With the sacrificial layer 120, the flexible patch layer 130 can be separated from the mold 110 without damage, obtaining the flexible patch 10 with high quality.

The mold 110 is configured such that it is not etched by an etching solution, even when a predetermined heat is applied, it can maintain the shape, and it has a predetermined rigidity. Additionally, the mold 110 is made of a non-magnetic material. In an example, the mold 110 may be made of a material including silicon (Si), but is not limited thereto, and may be made of various materials that are not removed by a material that removes the underlying sacrificial layer 120, can maintain the shape even at a particular temperature or above, and is not difficult to manufacture the mold.

Figure 3A:
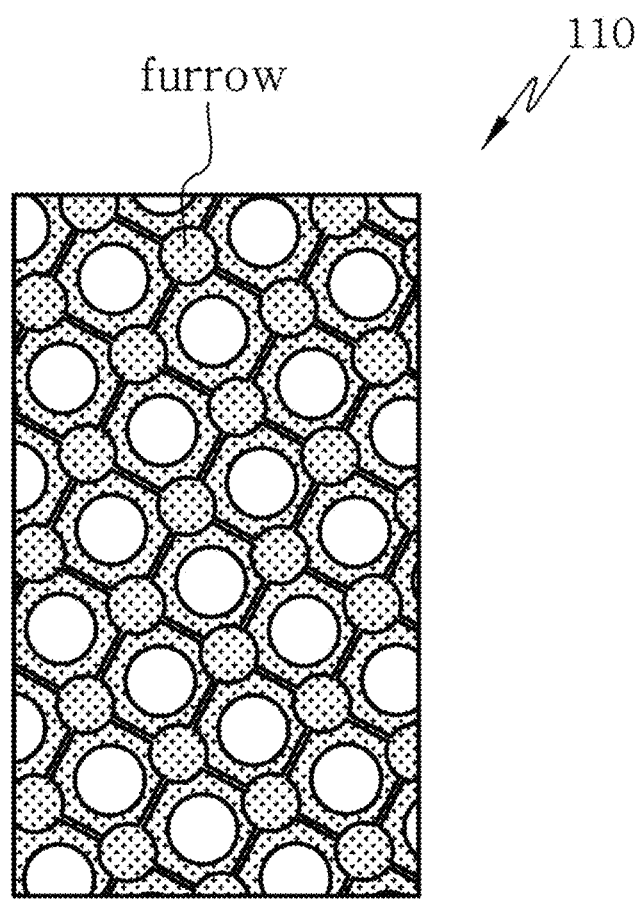
FIG. 3A is a diagram showing a geometric plane of a flexible patch having a plurality of holes, according to a first embodiment of the present disclosure.
Figure 3B:
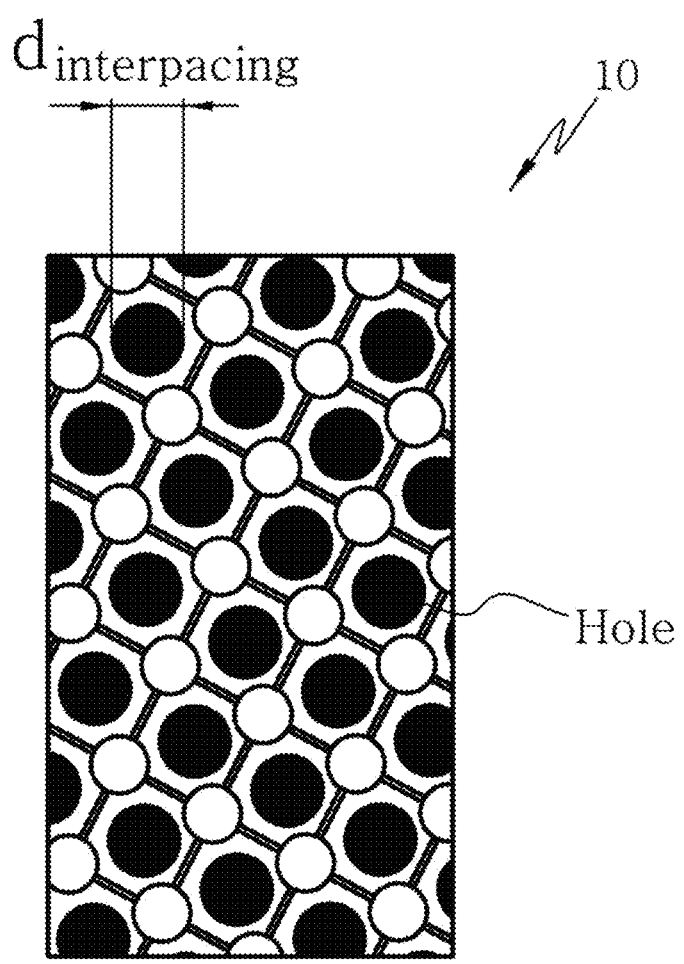
FIG. 3B is a diagram showing a geometric plane of a mold used to form the geometric plane of FIG. 3A, according to a second embodiment of the present disclosure.

FIG. 3A is a diagram showing the geometric plane of the mold used to form the through-hole pattern of FIG. 1, according to the first embodiment of the present disclosure, and FIG. 3B is a diagram showing the geometric plane of the flexible patch having the plurality of holes, according to the first embodiment of the present disclosure.

The mold 110 has the furrow shape and distribution to allow hole generation for the improved properties of the flexible patch 10 such as air permeability and adhesiveness. In an embodiment, the plurality of furrows formed on the surface of the mold 110 may be configured to form a circular hole pattern. Referring to FIG. 3A, the mold 110 having a plurality of furrows of circular border may be used to form the plurality of holes in the flexible patch 10. That is, the mold 110 has a structure in which a pillar is formed around a circular empty space. Using the mold 110 of FIG. 3A, the flexible patch 10 including through-holes having the plane of FIG. 3B may be obtained.

Additionally, considering the design of the semiconductor circuit that will be integrated onto the flexible patch 10, the furrows may be formed on the surface of the mold 110. In certain embodiments, the plurality of furrows formed on the surface of the mold 110 forms a circular hole pattern, and the circular hole pattern may include a combination of a circular hole having a larger diameter, and a plurality of circular holes having a smaller diameter, surrounding the circular hole.

In an embodiment, the plurality of furrows formed in the mold 110 may be distributed such that the spacing between the holes of the flexible patch 10 is less than 60 μm. The sweat pores have various sizes depending on the position on the skin. For example, it is known that the area of the sweat pores has the diameter of 60 μm or more, and has the diameter of 80 μm on average. Additionally, biological functions performed by sweat such as adjustment of the quantity of waste to excrete and the temperature are different depending on the position on the skin, and the distribution density differs in each body part. For example, the sweat pores are distributed at the density of 60 $cm^{-2}$ on the back, 400 $cm^{-2}$ on the palm, and 180 $cm^{-2}$ on the forehead.

Based on the information associated with the size and area of sweat pores, the spacing between the holes of the flexible patch 10 should be less than 60 μm. When the spacing between the holes is equal to or larger than 60 μm, the surface of the flexible patch 10 other than the holes may block the sweat pores. Accordingly, the flexible patch 10 having the spacing between the holes of less than 60 μm may have higher air permeability (e.g., nearly 100% air permeability). In certain embodiments, the flexible patch 10 may be manufactured using the mold 10 which makes a through-hole pattern having the spacing between the holes of 50 μm.

The main factor for obtaining high air permeability is the spacing between the through-holes. The size of the through-hole affects both adhesiveness and air permeability. It is because as the size of the through-hole is larger, the skin area that contacts air increases, but on the contrary, the volume of skin held reduces. The embodiments of the present disclosure can obtain high air permeability and strong adhesiveness by reducing the spacing between the through-holes even though the size of the through-hole is small. The size of the through-hole may be variously set within the range in which adhesiveness is not hindered.

In an embodiment, the size of the hole may be set based on the design of the semiconductor circuit that will be disposed on the flexible patch 10. For example, when parts of a piezoelectric device are disposed on the through-holes on the flexible patch 10 and the circuit elements are disposed to measure and transmit changes in electric current with the deformation of the piezoelectric device, it may be set such that parts of the piezoelectric device where deformation usually occurs have larger through-holes, and the remaining parts have smaller through-holes. In this case, only a small number of through-holes, where the piezoelectri device is disposed, has a large size, and the remaining through-holes occupying most of the flexible patch 10 have a sufficiently small size in which the skin is held, and thus the flexible patch 10 still has strong adhesiveness.

Referring back to FIG. 2, the sacrificial layer 120 is made of a material that can be used to manufacture nano-scale or micro-scale semiconductor devices. In an embodiment, the sacrificial layer 120 is made of a material including poly (methyl methacrylate) (PMMA). However, the sacrificial layer 120 is not limited thereto, and may be made of a material including polymer.

In an embodiment, the sacrificial layer 120 is formed on one surface of the mold 110 having the concave furrows by a spin coating method (S110). The sacrificial layer 120 is formed with a thickness that can prevent the adhesion between the mold 110 and the flexible patch layer 130, and can be easily removed by the etching solution in S170.

The flexible patch layer 130 is made of a material having flexible properties to allow conformable contact so that the shape of the patch can deform along the skin contour, and having adhesiveness enough to adhere to skin. In an embodiment, the flexible patch layer 130 may be made of elastomer having similar mechanical properties to skin. In an example, the flexible patch layer 130 may be made of a material including poly-dimethylsiloxane (PDMS). When the flexible material having similar mechanical properties (e.g., elastic modulus, Poisson's ratio) to skin is used, an interfacial mechanical mismatch does not occur when the flexible patch 10 adheres to skin, and accordingly, buckling and delamination do not occur in the patch, damage does not occur in the patch and adhesiveness reduction caused by buckling and delamination does not occur, so the flexible patch 10 has strong adhesiveness.

In certain embodiments, the flexible patch layer 130 may be formed with a predetermined thickness. When the thickness of the flexible patch layer 130 is too small, durability enough to adhere to skin repeatedly several times may not be obtained. In an example, the flexible patch layer 130 may be formed with the thickness of 75 μm or more.

The details of the flexible patch layer 130 relating to the thickness, structure and other properties of the flexible patch layer 130 will be described in more detail with reference to FIGS. 4 and 5.

In forming the flexible patch layer 130 on the sacrificial layer 120 (S130), the flexible material (e.g., PDMS) that forms the flexible patch layer 130 fills the furrows. The flexible material fills the furrows, and further, may flood out of the furrows. When a larger amount of flexible materials than the internal volume of the furrows is supplied and the flexible material floods out of the furrows, a portion of the flexible patch layer 130 may be formed at a higher position than the surface of the mold 110.

The structure including the mold 110, the sacrificial layer 120 and the flexible layer 130, obtained by filling or flooding the furrows with the flexible material is, for example, similar to a structure in which a cast is poured into the mold before completing a cast product. Hereinafter, to help a understanding of those skilled in the art, the cast-mold structure used herein refers to a structure including the mold 110, the sacrificial layer 120 and flexible material 130, in which the flexible material fills the furrows (or floods the furrows) as shown in S130 of FIG. 2, and the flexible material may be soft or rigid.

After the flexible patch layer 130 is formed, the flexible patch layer 130 (i.e., formed at the higher position than the surface of the mold 110) exceeding the furrows is removed (S150). In an embodiment, the flexible patch layer 130 region (i.e., excessive surface) exceeding the furrows of the mold 110 contacts a board 150, and the board 150 and/or the flexible patch layer 130 (i.e., the cast-mold structure) is rubbed to remove the region exceeding the furrows.

The board 150 serves as a plastering board that rubs to remove the flexible material of the excessive region. In an embodiment, the board 150 includes a substrate 151 and a sacrificial layer 152 formed on the substrate 151. The substrate 151 may have a structure (e.g., a flat structure) suitable for performing a rubbing function, durability and rigidity. Additionally, the substrate 151 may be made of a non-magnetic material. In an example, the substrate 151 may be made of a material including silicon (Si).

The sacrificial layer 152 may be made of a material that can be etched by the etching solution in S170. In an example, the sacrificial layer 152 may include the same material (e.g., PMMA) as the sacrificial layer 120 as shown in FIG. 2. However, the sacrificial layer 152 is not limited thereto, and may be made of a material that can be etched by the etching solution in S170 and minimizes damage that may occur on the surface of the flexible patch layer 130 after removal in the process of rubbing in contact with the flexible patch layer 130 region exceeding the furrows.

In an embodiment, the sacrificial layer 152 may be formed on the substrate 151 by a spin coating method, but is not limited thereto, and may be formed on the substrate 151 by various coating methods.

The rubbing process in S150 may further include an additional process to remove the excessive region more efficiently.

In an embodiment, S150 may include heating the contact region between the flexible patch layer 130 and the board 150. For example, the flexible material of the region exceeding the furrows of the mold may be removed more efficiently by applying heat of 70° C. or above to the contact region between the flexible patch layer 130 and the board 150.

When heat is applied to the flexible patch layer 130 or the contact region, the rigidity of the contact region is weakened (i.e., having a soft structure state). Accordingly, when rubbing the board 150 against the flexible patch layer 130 (i.e., the cast-mold structure) (or when rubbing the cast-mold structure against the board 150), the flexible material of the exceeding region spreads out of the area occupied by the cast-mold structure by relative movements. For example, it is similar to a phenomenon that when putting a support plate on plaster and rubbing, the plaster under the support plate spreads out of the area occupied by the support plate. Eventually, the height of the excessive region gradually becomes lower, and as shown in FIG. 2, the topmost of the flexible material filled in the furrows is on a level with the surface where the furrows are formed.

In an embodiment, S150 may include flipping so that the flexible patch layer 130 is disposed on one surface of the board 150 in the course of contact. After flipping is performed, the flexible patch layer 130 (i.e., the cast-mold structure) is disposed on one surface of the board 150. In the above embodiment, the area of the board 150 may be larger than the area of the cast-mold structure.

In this placement, when rubbing the board 150 and the cast-mold structure, the flexible material of the excessive region spreads out of the area occupied by the cast-mold structure by movements of the cast-mold structure, and there is a lower probability that the flexible material of the excessive region will remain on the side of the cast-mold structure.

In an embodiment, S150 may further include applying the pressure to the contact region between the flexible patch layer 130 and the board 150. The pressure may be applied using a magnet as shown in FIG. 2. In an example, the cast-mold structure and the board 150 may be disposed in contact between a magnet 161 and a magnet 162. Accordingly, the pressure may be applied to the contact region by attracting forces between the magnet 161 and magnet 162. As described above, the cast-mold structure and the board 150 may be made of a non-magnetic material, and do not affect the interaction of attaching forces occurring between the magnet 161 and the magnet 162. As a result of rubbing the cast-mold structure and the board 150, the time taken to remove the excessive region may be reduced, thereby improving the efficiency of the removal process.

After S150, the sacrificial layer 120 is etched using an etching solution in S170. The etching is performed with the controlled selectivity of the etching solution to etch the sacrificial layer 120 while not etching the mold 110 and the flexible patch layer 130. In an embodiment, the etching solution used to etch the sacrificial layer 120 may include acetone.

In an experimental embodiment, the cast-mold structure, from which the region of the flexible patch layer 130 exceeding the furrows has been removed, is dipped in the etching solution to remove the sacrificial layer 120, and the cast (i.e., the flexible patch layer 130) is separated from the mold 110. The separated flexible patch layer 130 includes a plurality of holes formed by the furrows of the mold 110. Because the flexible material in the furrows is on a level with the surface of the mold 110 in S150, the plurality of holes is formed of penetrating type. As a result, as shown in FIG. 2, the flexible patch layer 130 including the plurality of through-holes can be obtained, and the flexible patch layer 130 including the plurality of through-hole may be used as the flexible patch 10.

The time during which the cast-mold structure is dipped in the etching solution may be variously set. For example, the etching time of the cast-mold structure may be determined by the thickness of the furrow (i.e., the thickness of the flexible patch 10), the thickness of the sacrificial layer 120, and the cross sectional area of contact between the furrow and the flexible patch layer 130.

Additionally, for more efficient etching process in S170, ultrasonic treatment may be performed on the cast-mold structure in the etching solution.

Although the flexible patch 10 manufactured by S110 to S170 is manufactured with the micro scale thickness, adhesiveness may be increased by the plurality of holes. Additionally, the plurality of holes is a penetrating hole, and after the flexible patch 10 adheres to skin, the skin of the adhered region is not isolated from the external air. Accordingly, the flexible patch 10 can have both air permeability and adhesiveness, dissimilar to the conventional skin patch surface-treated such that only the patch surface has a micro structure (such as, for example, octopus suckers or gecko feet) and thus only adhesiveness is good and air permeability is relatively low.

Additionally, when the flexible patch layer 130 is separated from the mold 110 using the sacrificial layer 120, damage such as tear does not occur in the process of generating a plurality of holes (or a hole pattern) in the flexible patch layer 130 and separating the flexible patch layer 130.

The flexible patch 10 has very good adhesiveness to skin and air permeability, and thus can be used to manufacture a variety of skin-adherable electronic devices such as skin sensors.

In addition, the flexible patch 10 may have stronger adhesiveness by the material properties such as the components and thickness of the flexible patch layer 130.

FIGS. 4A to 4D are diagrams illustrating adhesiveness of the flexible patch 10 that adheres to skin, according to an embodiment of the present disclosure.

The through-holes of the flexible patch 10 are on micro scale, and because they are very small compared to the size of the flexible patch 10, they are omitted in FIG. 4 for clarity of description.

Figure 4A:
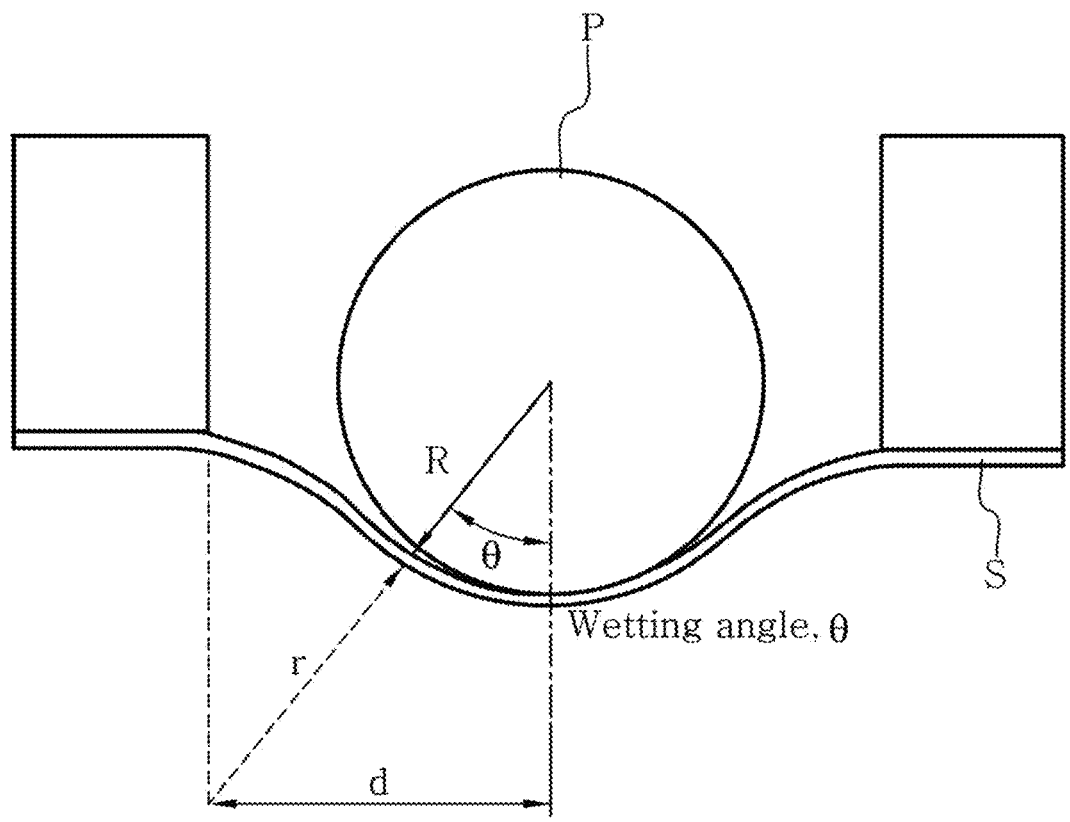
FIGS. 4A to 4D are diagrams illustrating adhesiveness of a flexible layer of a bi-layer structure that adheres to skin, according to a first embodiment of the present disclosure.

FIG. 4A is a diagram illustrating an adhesion principle between an object and a surface.

An ability of the object P that contacts the surface S to adhere to the surface S is determined by competition of structural resistance to deformation and interfacial interaction (competition in terms of reversibility and pluripotency). As shown in FIG. 4A, when the surface is deformed by the object P, energy between the object P and the surface S may be expressed by the following Equation 1-4.

$$U_{total} = U_{adhesion} + U_{Bending} \qquad [\text{Equation 1}]$$

$$U_{adhesion} = -WbR(2\theta) \qquad [\text{Equation 2}]$$

$$U_{Bending} = +\frac{bD\theta}{12R} \qquad [\text{Equation 3}]$$

$$D = Et^3 \qquad [\text{Equation 4}]$$

Here, $U_{total}$ denotes the total potential energy, $U_{adhesion}$ denotes adhesion energy between the object P and the surface S, and $U_{bending}$ denotes bending energy associated with the resistance of the surface S deformed by the object P. Here, the symbols for adhesion energy and bending energy merely indicate the direction of interaction, and in another embodiment, the symbol for the adhesion energy may be indicated by +, and the symbol for the bending energy may be indicated by −.

Additionally, W denotes the work of adhesion (Unit: N m$^{-1}$), b denotes the length of the object P adhered to the surface, R denotes the curvature, and θ denotes the contact angle which is an angle from the center of the contact region between the object P and the surface S to the point where the contact region ends. D is the flexural rigidity for the object P, and is determined by the elastic modulus (Young's modulus) of the object P and the thickness of the object.

To describe adhesiveness of the flexible patch 10 more simply, the case in which the flexible patch 10 of a monolayer structure adheres to the skin surface is described with reference to FIG. 4A.

When the case in which the flexible patch 10 adheres to the skin surface is applied to FIG. 4A, the surface S corresponds to the skin surface, and the object P corresponds to the flexible patch 10 including the flexible patch layer 130 having the through-holes. Accordingly, the flexural rigidity D for the flexible patch 10 is determined by the elastic modulus E of the flexible patch layer 130 and the thickness t of the flexible patch layer 130.

When adhesion energy is equal to or higher than bending energy, adhesion between the patch 10 and the skin surface is possible. When adhesion energy is less than bending energy, the patch 10 is detached from the skin surface. The critical work of adhesion $W_C$ that determines to be adherable or not is determined by the following Equation 5.

$$\frac{dU_{total}}{d\theta} = -2W_c bR + \frac{bD}{12R} = 0 \qquad \text{[Equation 5]}$$

When writing Equation 5 by $W_C$, the critical work of adhesion $W_C$ at which adhesion between the object and the surface maintains is calculated as $W_C=D/(24R^2)$. When the work of adhesion W between the flexible patch 10 and the skin surface is equal to or greater than the critical work of adhesion $W_C$, the flexible patch 10 can make a conformal contact with the skin surface. In contrast, when the work of adhesion W between the flexible patch 10 and the skin surface is less than the critical work of adhesion $W_C$, the flexible patch 10 does not contact the skin surface. Accordingly, to make adhesion between the flexible patch 10 and the skin surface possible, it is necessary that the magnitude of the critical work of adhesion $W_C$ reduces, and/or the magnitude of the work of adhesion W between the flexible patch 10 and the skin surface increases.

Referring to Equation 4, when the patch 10 is made of a material having a high elastic modulus (e.g., a stiff material), and/or the thickness is large, the patch 10 has high flexural rigidity D. Accordingly, when the flexural rigidity D of the flexible patch 10 is low, and/or the work of adhesion between the skin surface and the flexible patch 10 is high, the flexible patch 10 can stably adhere to the skin surface.

In case that the elastic modulus E of the flexible patch 10 is low, when the thickness of the flexible patch 10 is small, the flexible patch 10 can stably adhere to the skin surface.

Additionally, the higher the adhesion energy between the flexible patch 10 and the skin surface, the stronger the adhesiveness of the flexible patch 10. Referring to Equation 2, adhesion energy between the skin surface and the flexible patch 10 relies on the work of adhesion W. The work of adhesion W between the flexible patch 10 and the skin surface is expressed by the following Equation 6.

$$W = \frac{4\gamma_{dPatch}\gamma_{dskin}}{\gamma_{dPatch} + \gamma_{dskin}} + \frac{4\gamma_{pPatch}\gamma_{pskin}}{\gamma_{pPatch} + \gamma_{pskin}} \qquad \text{[Equation 6]}$$

Here, $\gamma_d$ denotes the dispersive component of the contact surface, and $\gamma_p$ denotes the polar component of the contact surface. $\gamma_{dSkin}$ denotes the dispersive component of the contact surface of the skin, $\gamma_{dPatch}$ denotes the dispersive component of the contact surface of the patch 10, $\gamma_{pSkin}$ denotes the polar component of the contact surface of the skin, and $\gamma_{pPatch}$ denotes the polar component of the contact surface of the patch 10. The flexible patch 10 is formed based on the above Equation 6.

As described above, the flexible patch 10 may be used to manufacture skin sensors. The PDMS patch 10 having the exemplary elastic modulus of 1 MPa enough to support micro scale ultra-small devices in the micro thickness range can adhere to the skin. $\gamma_d$ and $\gamma_p$ of the skin surface may be different for each part, but the maximum and minimum ranges of the variables are known as shown in the following Table 1.

TABLE 1

| mNm$^{-1}$ | $\gamma_d$ | $\gamma_p$ |
|---|---|---|
| Skin Max | 40 | 8 |
| Skin Min | 11.7 | 1.7 |
| PDMS (E = 1 MPa, t = 1 mm) | 19.1 | 0.5 |

When applying data of the above Table 1 to the above Equation 6, the work of adhesion W between the skin and the PDMS patch 10 is roughly calculated as follows: $31 \leq W \leq 54$ mJ m$^{-2}$.

To adhere the thickness of the PDMS patch 10 having the elastic modulus of 1 MPa to all types of skins, it should be able to adhere to skin surface having the lowest work of adhesion (Skin Min). Accordingly, the PDMS patch 10 should have the value of $W_C=31$. Accordingly, when the PDMS patch 10 is formed with the thickness of about 80 μm, the critical work of adhesion $W_C$ requirement is satisfied. Accordingly, when the single flexible patch 10 of 1 MPa is manufactured with the thickness of less than 80 μm, conformal adhesion to skin surface is possible.

In some embodiments, when the single flexible patch 10 having the elastic modulus lower than 1 MPa has the thickness of less than 80 μm, it may have stronger adhesiveness. In other embodiments, one layer of the flexible patch 10 having the elastic modulus lower than 1 MPa can make a conformable contact with the skin surface at the thickness of 80 μm or more. For example, even when the thickness of one layer that adheres to the skin surface is 100 μm, it can adhere to the skin.

As described above, the flexural rigidity D is associated with the ability of the flexible patch 10 to adhere, and is also associated with the ability of the flexible patch 10 to maintain the shape. Referring to the above Equations 4 and 5, in case that the elastic modulus E of the flexible patch 10 is low, when the thickness of the flexible patch 10 is small, the flexible patch 10 can stably adhere to the skin surface.

However, when the thickness of the flexible patch 10 is too small or the flexible patch 10 is formed with too low elastic modulus, considering only adhesiveness, it is difficult to handle. Specifically, when the flexural rigidity of the flexible patch 10 is too low, the flexible patch 10 is bent, making it difficult to handle, and it is difficult to uniformly maintain the shape of the flexible patch 10. Accordingly, when the flexural rigidity of the flexible patch 10 is too low, it is difficult to integrate other elements on the flexible patch 10.

To overcome this problem, the flexible patch 10 may be configured such that a region that adheres to skin has lower flexural rigidity, and a region that does not adhere to skin and thus has a lower need for high adhesiveness, and where other elements are integrated, has flexural rigidity enough to maintain the shape without being subjected to bending. For example, the flexible patch 10 may be formed as one or more layers to have stronger adhesiveness and flexural rigidity enough to support other elements (for example, including electrodes, semiconductor devices, interactions, etc.). To manufacture the flexible patch 10, the flexible patch layer 130 that is formed on the sacrificial layer 120 may include one or more sub-layers.

Figure 4B:
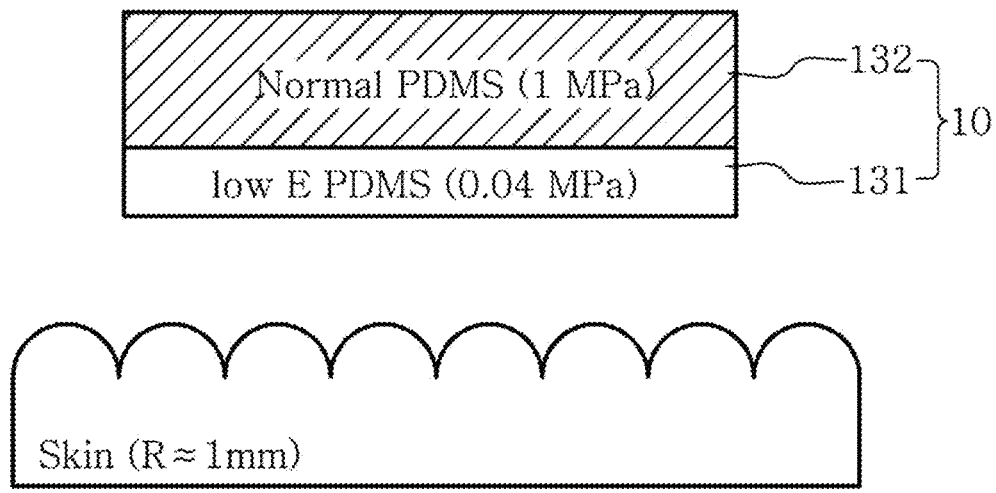

FIG. 4B is a diagram illustrating the flexible patch 10 of bi-layer structure having different elastic moduli according to an embodiment of the present disclosure.

In an embodiment, the flexible patch 10 having a bi-layer structure may include two sub-layers (a first flexible layer 131, and a second flexible layer 133 in FIG. 4B) with different rigidities. Here, the first flexible layer 131 that adheres to skin has a lower flexural rigidity D1 than the flexural rigidity D2 of the second flexible layer 132 that does not adhere to skin. For example, as shown in FIG. 4B, the first flexible layer 131 has the elastic modulus E1 of 0.04 MPa, and the second flexible layer 132 has the elastic modulus E2 of 1 MPa, and thus the first flexible layer 131 may be more softer.

In an embodiment, the flexible patch layer 130 may include the first flexible layer 131 and the second flexible layer 132 including a pre-polymer and a curing agent. Here, the second flexible layer 132 may have a higher ratio of curing agent than the ratio of curing agent of the first flexible layer 131. For example, the first flexible layer 131 may have a ratio of the pre-polymer and the curing agent of 40:1, and the second flexible layer 132 may have a ratio of pre-polymer and the curing agent of 10:1. Due to this ratio difference of the curing agent, the flexural rigidity D of the first flexible layer 131 and the second flexible layer 132 is differently determined.

By this difference in constituent material, the first flexible layer 131 is softer and stickier than the second flexible layer 132, allowing the flexible patch 10 to adhere to the skin. When the flexible patch 10 is used to manufacture a skin sensor, the more rigid second flexible layer 132 serves as a support (e.g., a substrate) for integration of micro scale devices.

Additionally, the first flexible layer 131 and the second flexible layer 132 may be formed with different thicknesses. Referring back to the above Equation 4, the flexural rigidity D is determined dependent on the elastic modulus E and the thickness.

Figure 4C:
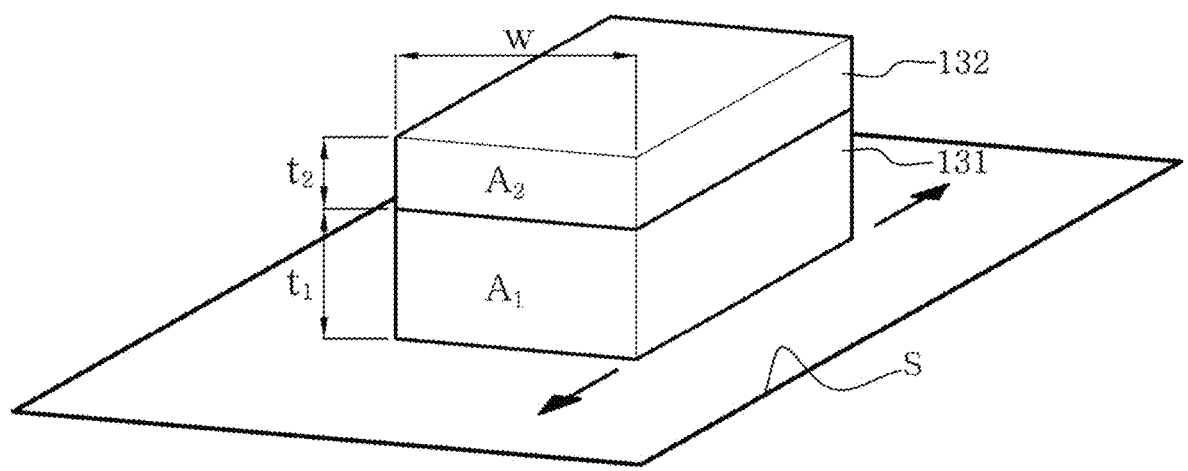
Figure 4D:
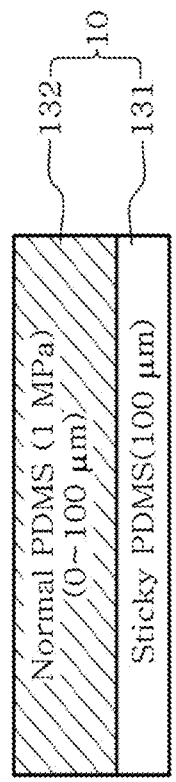
Figure 4D:
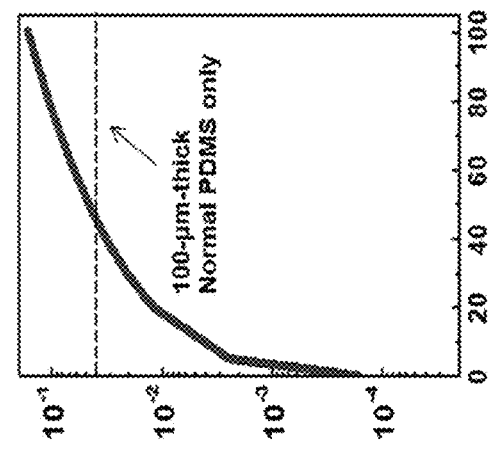
Figure 4D:
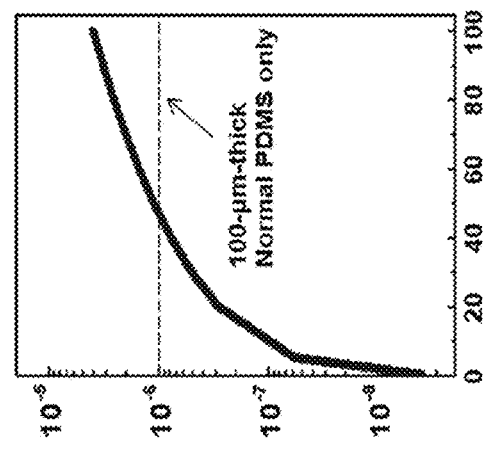
Figure 4D:
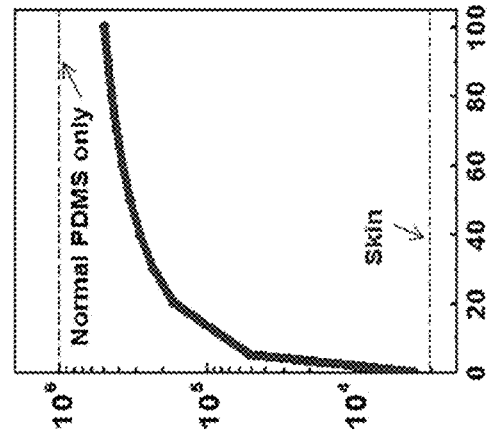

FIG. 4C is a diagram illustrating the flexible patch 10 of bi-layer structure having different thicknesses, according to the first embodiment of the present disclosure, and FIG. 4D is a diagram illustrating a graph showing the characteristics of the flexible patch as a function of the thickness of the bi-layer structure, according to the first embodiment of the present disclosure.

In an embodiment, the first flexible layer 131 that adheres to skin may be formed. For example, the first flexible layer 131 may have a low elastic modulus (e.g., 0.04 Mpa) to allow conformable adhesion to skin surface.

Additionally, to support the integrated semiconductor circuits on the flexible patch 10 and properly control the bending of the flexible patch 10 to make handling easy, the second flexible layer 132 may be more rigid. For example, the second flexible layer 132 may have a higher elastic modulus (e.g., 1 MPa) than the elastic modulus of the first flexible layer 131.

As shown in FIG. 4C, when the flexible patch 10 of bi-layer structure adheres to skin surface, generally, due to the nature of skin surface having a curved structure, the adhered flexible patch 10 is expanded. A restoring force $F_{ret}$ that tends to return to a state before expansion is applied to the expanded flexible patch 10. The restoring force $F_{ret}$ may be analyzed as shown in the following Equation 7. When the first flexible layer 131 and the second flexible layer 132 of the flexible patch 10 are made of the same material (e.g., PDMS), they may have the same tensile stress G and tensile strain £.

$$F_{ret} = F_1 + F_2 = w\epsilon(t_1 E_1 + t_2 E_2) \quad \text{[Equation 7]}$$

Here, F1 denotes the restoring force that is applied to the first flexible layer 131 adhered to skin, and F2 denotes the restoring force that is applied the second flexible layer 132 adhered to skin. t1 denotes the thickness of the first flexible layer 131, and t2 denotes the thickness of the second flexible layer 132.

The total elastic modulus Eeq of the flexible patch 10 of bi-layer structure may be expressed by the following Equation 8.

$$E_{eq} = \frac{F_{ret}/w(t_1 E_1 + t_2 E_2)}{\epsilon} = \left(\frac{t_1}{t_1 + t_2}\right) E_1 + \left(\frac{t_2}{t_1 + t_2}\right) E_2 \quad \text{[Equation 8]}$$

In an example, when the first flexible layer 131 having the elastic modulus of 0.04 MPa that adheres to skin is formed with the thickness of 100 μm, the graph of the effective elastic modulus and the flexural rigidity of the flexible patch 10, and the critical work of adhesion between the flexible patch 10 and the skin surface may be calculated by the above Equation 8, and the results are shown in FIG. 4D.

The first flexible layer 131 and the second flexible layer 132 included in the flexible patch 10 of bi-layer structure may be formed to have a suitable thickness and elastic modulus for the function of a product (e.g., a skin sensor) for which the flexible patch 10 is used, with reference to the above Equation 8.

The above description of the flexible patch layer 130 of bi-layer structure is for illustration only, and it is not interpreted that the flexible patch layer 130 of the present disclosure is limited to a bi-layer structure. In other embodiments, the flexible patch layer 130 may be formed with a mono-layer and a triple-layer structure. In an example, the flexible patch layer 130 may be formed with a mono-layer structure including only the second flexible layer 133. In another example, the flexible patch layer 130 may be formed with a triple-layer structure including a rigid second flexible layer between two soft first flexible layers. The flexible patch layer 130 of triple-layer structure may include two first flexible layers having different thicknesses. For example, the first flexible layer of the region that adheres to skin may be formed with the thickness of 10 μm, and the first flexible layer on the opposite side may be formed with the thickness of 100 μm.

Additionally, 1 MPa disclosed as the elastic modulus for supporting the micro device on micro scale is only for illustration purposes, and the second flexible layer 132 included in the flexible patch 10 may have a different elastic modulus.

Accordingly, as the flexible patch 10 is manufactured using the sacrificial layer 120, damage does not occur in the process of obtaining the flexible patch layer 130 of micro scale thickness, and thus the flexible patch 10 can have high durability.

Additionally, because of having a plurality of through-holes and one or more multi-layer structures, the flexible patch 10 can obtain good air permeability and adhesiveness.

Second Embodiment

Figure 5:
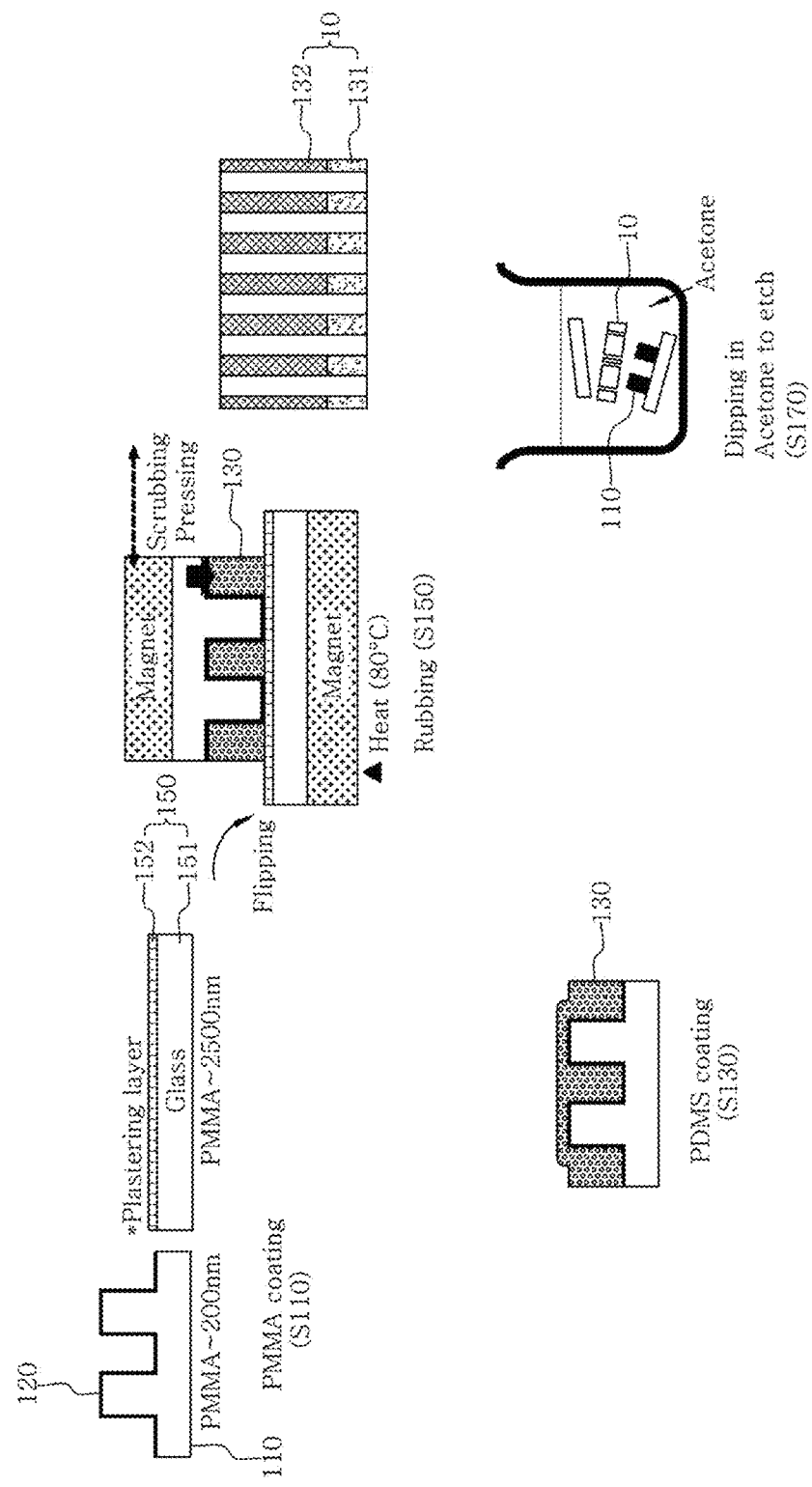
FIG. 5 is an exemplary conceptual diagram of a method for manufacturing a flexible patch having a geometric plane associated with an auxetic structure property, according to a second embodiment of the present disclosure.

FIG. 5 is an exemplary conceptual diagram of a method for manufacturing a flexible patch having a geometric plane associated with an auxetic structure property, according to a second embodiment of the present disclosure.

Referring to FIGS. 2 and 5, the method for manufacturing a flexible patch according to the second embodiment of the present disclosure is so much similar to the flexible patch method according to the first embodiment of FIG. 2, and difference(s) will be mainly described below.

The flexible patch 10 may have higher air permeability and/or stronger adhesiveness by the structure of the mold 110 that determines the shape, distribution and pattern of holes formed in the flexible patch 10.

Figure 6A:
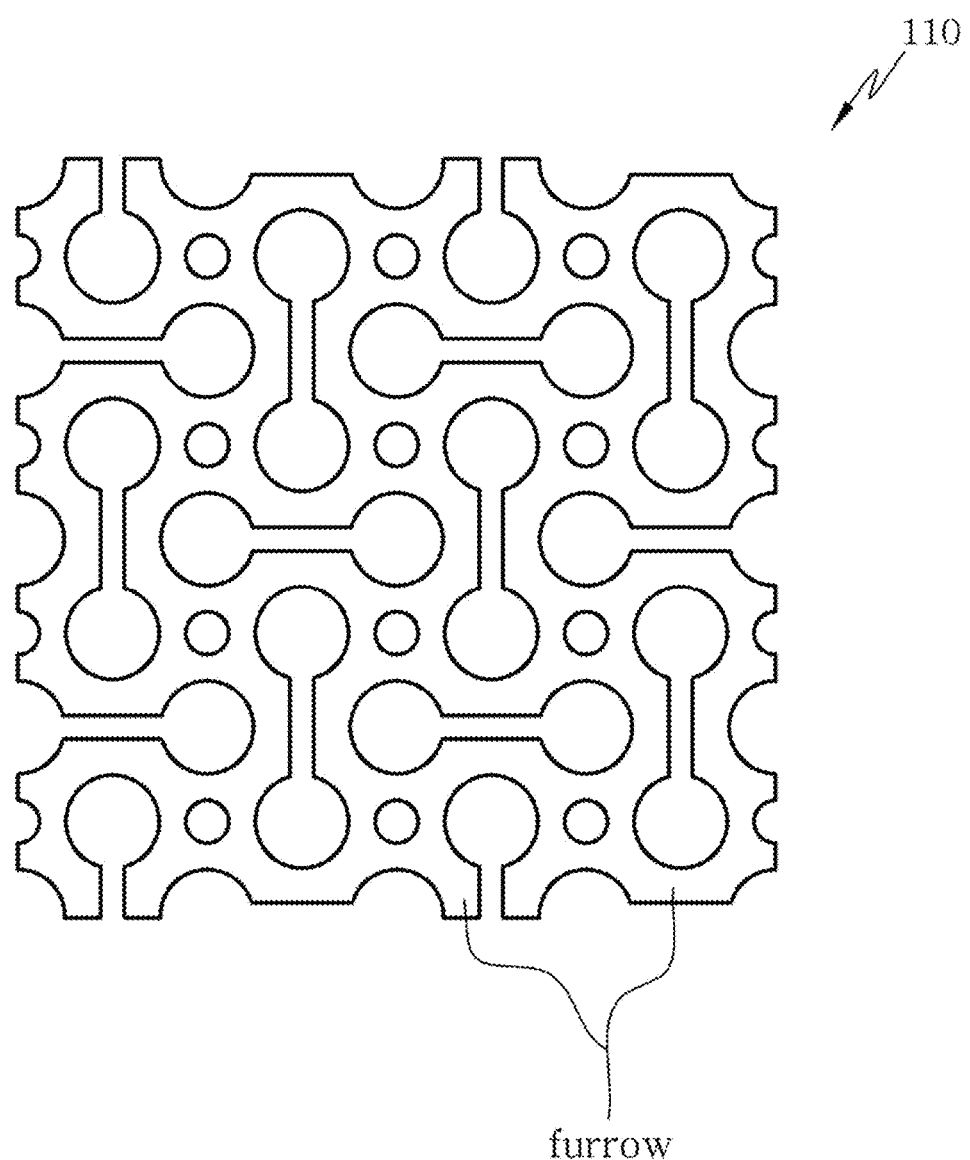
FIG. 6A is a diagram showing a geometric plane of a flexible patch that can implement an auxetic structure property, according to a second embodiment of the present disclosure.
Figure 6B:
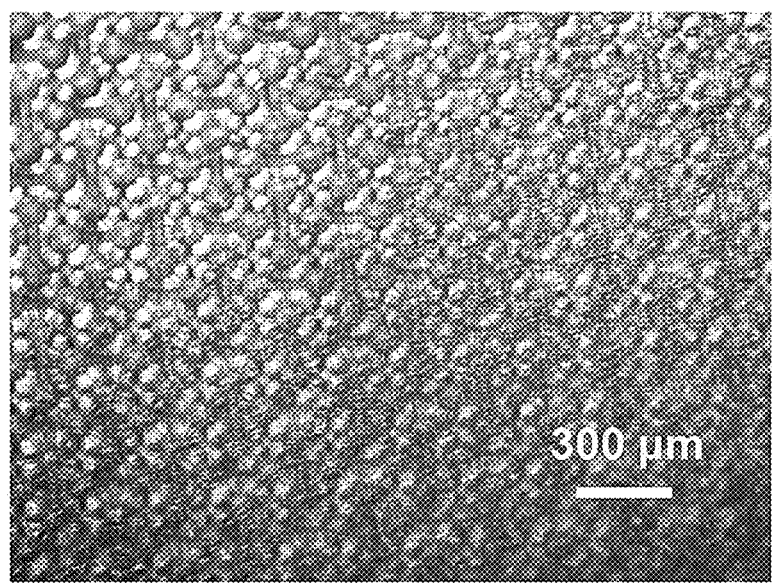
FIG. 6B is a diagram showing a geometric plane of a mold used to form the geometric plane of FIG. 6A, according to a second embodiment of the present disclosure.

FIG. 6A is a diagram showing the geometric plane of the mold used to form the geometric plane of FIG. 6A, according to the second embodiment of the present disclosure, and FIG. 6B is a diagram showing the geometric plane of the flexible patch that can implement an auxetic structure property, according to the second embodiment of the present disclosure.

In the second embodiment, the flexible patch 10 may further include a plurality of through-holes having a dumbbell-shaped plane. In this case, the flexible patch 10 may have a property (i.e., an auxetic structure property) resulting from the auxetic structure.

In general, an auxetic structure refers to a structure that, when it is placed under tension in a first direction, increases in its dimensions in a direction that is orthogonal to the first direction. For example, if the auxetic structure can be described as having a length, a width and a thickness, then when the auxetic structure is under tension longitudinally, it increases in width. Additionally, the auxetic structure is bi-directional such that it increases in length and width when stretched longitudinally, and increases in width and length when stretched laterally, but does not increase in thickness. This auxetic structure characterized by having a negative Poisson's ratio.

As shown in FIG. 6A, when the flexible patch 10 has circular holes and dumbbell-shaped holes including circles at two ends and a middle connecting the circles at two ends in the form of a pillar with a smaller thickness than the diameter of the two ends (i.e., dumbbell-hole pattern of through-holes), the flexible patch 10 having the through-holes may have the auxetic structure property. That is, the mold 110 is formed with a structure having a pillar surrounding a circular and/or dumbbell-shaped empty space. Using the mold 110 of FIG. 6A, the flexible patch 10 including the through-holes having the plane of FIG. 6B may be obtained.

In an embodiment, to obtain high air permeability, the spacing between holes may be less than 60 μm as described above. In an example, as shown in FIG. 6A, the spacing between the center of a connector of a dumbbell through-hole $H_C$ and one end of another dumbbell through-hole $H_C$ may be 35 μm, and the spacing between one end of a dumbbell through-hole $H_C$ and another circular through-hole $H_B$ may be 25 μm. Additionally, the diameter of the circular through-hole $H_B$ may be 50 μm, and the inner spacing of one end of the dumbbell through-hole $H_C$ may be 100 μm. However, this is for illustration purposes only, and may be variously set based on air permeability, adhesiveness and durability of the flexible patch 10.

To manufacture the flexible patch 10 having the auxetic structure property, the method for manufacturing the flexible patch 10 according to the second embodiment includes forming a sacrificial layer 120 on a mold 110 having a plurality of furrows that can form dumbbell-shaped holes and circular holes (S110), as shown in FIG. 5.

Referring back to FIG. 2, to manufacture the flexible patch 10 having holes formed at a few tens of micro scale of spacing such as, for example, 60 μm, a sacrificial layer 120 may be formed (S130). However, when S130 method of FIG. 2 is applied to the second embodiment, it is impossible to separate the PDMS patch layer 130 from the mold 110. This is because the mold 110 is configured to form circular and dumbbell through-holes, so the contact area between the mold 110 and the PDMS patch layer 130 increases as compared to the first embodiment, and the spacing of the mold 110 is narrower, resulting in unbalanced PMMA spin coating.

Accordingly, the method for manufacturing the flexible patch 10 according to the second embodiment includes forming the sacrificial layer 120 on the mold 110 using an evaporation coating method (S130) as shown in FIG. 5. In an example, the evaporation coating method may be self-assembled monolayers (SAMs). By use of the evaporation coating method, unbalanced coating does not occur, compared to than PMMA spin coating. Accordingly, the sacrificial layer 120 and the flexible patch layer 130 are formed on the mold 110 having the geometric plane associated with the auxetic structure property (S110, S130), the region of the flexible patch layer 130 exceeding the furrows is removed (S150), and the sacrificial layer 120 is etched to obtain the flexible patch 10 with the geometric plane having the auxetic structure property.

The flexible patch 10 according to the second embodiment causes about 6% of moisture change in comparison of changes in skin moisture before and after the flexible patch 10 is adhered to the skin. That is, even when the flexible patch 10 is adhered to the skin, a moisture loss of the skin hardly occurs.

The present disclosure has been hereinabove described with reference to the embodiments shown in the drawings, but this is provided for illustration purposes only and those having ordinary skill in the corresponding field will understand that various modifications and variations may be made thereto. However, it should be noted that such modifications fall within the technical protection scope of the present disclosure. Accordingly, the true technical protection scope of the present disclosure shall be defined by the technical spirit of the appended claims.

What is claimed is:

1. A method for manufacturing a skin-adherable flexible patch, comprising:
   forming a first sacrificial layer on a mold having a plurality of concave furrows on one surface;
   forming a flexible patch layer on the first sacrificial layer;
   contacting a board with the flexible patch layer, and rubbing the board or the flexible layer to remove a region of the flexible patch layer exceeding the furrows; and
   etching the first sacrificial layer to obtain a flexible patch having a plurality of holes.

2. The method for manufacturing a skin-adherable flexible patch according to claim 1, wherein in the removing the flexible patch layer, the board includes a substrate; and a second sacrificial layer formed on one surface of the substrate,
   the second sacrificial layer contacts the region of the flexible layer exceeding the furrows.

3. The method for manufacturing a skin-adherable flexible patch according to claim 1, wherein the removing the flexible patch layer further comprises heating the contact region.

4. The method for manufacturing a skin-adherable flexible patch according to claim 3, wherein the removing the flexible patch layer further comprises applying pressure to the contact region between the board and the region of the flexible layer exceeding the furrows.

5. The method for manufacturing a skin-adherable flexible patch according to claim 1, wherein the flexible patch layer is made of a material including poly-dimethylsiloxane (PDMS).

6. The method for manufacturing a skin-adherable flexible patch according to claim 1, wherein the forming the flexible patch layer comprises:
   forming a first flexible layer on the sacrificial layer; and
   forming a second flexible layer on the first flexible layer, the second flexible layer being more rigid than the first flexible layer.

7. The method for manufacturing a skin-adherable flexible patch according to claim 6, wherein a thickness (t1) of the first flexible layer and a thickness (t2) of the second flexible layer are determined based on the following Equation:

$$W \geq Wc \text{ where } Wc = E_{eq}t^3/(24R^2),$$

$$W = \frac{4\gamma_{dPatch}\gamma_{dskin}}{\gamma_{dPatch} + \gamma_{dskin}} \frac{4\gamma_{pPatch}\gamma_{pskin}}{\gamma_{pPatch} + \gamma_{pskin}},$$

$$E_{eq} = \left(\frac{t_1}{t_1 + t_2}\right)E_1 + \left(\frac{t_2}{t_1 + t_2}\right)E_2$$

$$t = t1 + t2,$$

where t denotes a thickness of the flexible patch, E1 denotes an elastic modulus of the first flexible layer, E2 denotes an elastic modulus of the second flexible layer, R denotes a curvature of the flexible patch adhered to the skin, $y_{dskin}$ denotes a dispersive component of contact surface of the skin, $y_{dPatch}$ denotes a dispersive component of contact surface of the patch, $y_{pSkin}$ denotes a polar component of contact surface of the skin, and $y_{pPatch}$ denotes a polar component of contact surface of the patch.

8. The method for manufacturing a skin-adherable flexible patch according to claim 1, wherein the forming the first sacrificial layer comprises forming the first sacrificial layer by spin coating, and
   the first sacrificial layer is made of a material including poly(methyl methacrylate) (PMMA), and a surface of the mold has furrows that can form circular through-holes.

9. The method for manufacturing a skin-adherable flexible patch according to claim 1, wherein the forming the first sacrificial layer comprises forming the first sacrificial layer by evaporation coating, and
   the first sacrificial layer is formed with a self-assembled monolayer (SAM) structure, and a surface of the mold has furrows that can form circular through-holes and dumbbell through-holes.

* * * * *